(12) United States Patent
Oomori et al.

(10) Patent No.: US 7,692,780 B2
(45) Date of Patent: Apr. 6, 2010

(54) SURFACE INSPECTING APPARATUS

(75) Inventors: Takeo Oomori, Tokyo (JP); Kazuhiko Fukazawa, Kamakura (JP)

(73) Assignee: Nikon Corporation, Tokyo (JP)

(\*) Notice: Subject to any disclaimer, the term of this patent is extended or adjusted under 35 U.S.C. 154(b) by 0 days.

(21) Appl. No.: 12/314,666

(22) Filed: Dec. 15, 2008

(65) Prior Publication Data
US 2009/0103080 A1  Apr. 23, 2009

Related U.S. Application Data

(63) Continuation of application No. PCT/JP2007/063538, filed on Jul. 6, 2007.

(30) Foreign Application Priority Data

Jul. 14, 2006 (JP) ............................ 2006-193490

(51) Int. Cl.
*G01N 21/00* (2006.01)
(52) U.S. Cl. .................................. 356/237.5
(58) Field of Classification Search .... 356/237.2–237.5
See application file for complete search history.

(56) References Cited

U.S. PATENT DOCUMENTS

| 6,774,987 | B2 | 8/2004 | Komatsu et al. | |
|---|---|---|---|---|
| 2004/0063232 | A1 | 4/2004 | Komatsu et al. | |
| 2005/0206888 | A1* | 9/2005 | Yoshida et al. | 356/237.5 |
| 2005/0280806 | A1* | 12/2005 | Oomori et al. | 356/237.2 |
| 2006/0072106 | A1* | 4/2006 | Matsui et al. | 356/237.5 |
| 2006/0098189 | A1* | 5/2006 | Oomori et al. | 356/237.5 |
| 2006/0192953 | A1 | 8/2006 | Fukazawa et al. | |
| 2006/0232769 | A1 | 10/2006 | Sugihara et al. | |

FOREIGN PATENT DOCUMENTS

| JP | U-5-30761 | 4/1993 |
|---|---|---|
| JP | A-10-232122 | 9/1998 |
| JP | A-2000-206050 | 7/2000 |
| JP | A-2006-105951 | 4/2006 |
| WO | WO 2005/040776 A1 | 5/2005 |

\* cited by examiner

*Primary Examiner*—Tarifur R. Chowdhury
*Assistant Examiner*—Isiaka O Akanbi
(74) *Attorney, Agent, or Firm*—Oliff & Berridge, PLC

(57) ABSTRACT

A surface inspecting apparatus is provided with an illuminating means for illuminating a repeated pattern formed on the surface of an object to be inspected by linear polarization; a setting means for setting an angle formed by a direction on the surface of an incidence plane of the linear polarization and a repeating direction of the repeated pattern at a prescribed value other than 0; an extracting means for extracting polarization components vertical to an oscillation surface of the linear polarization, from light generated in a specular direction from the repeated pattern; a light receiving means for receiving the light extracted by the extracting means, and outputting light intensity of the specular reflection light; and a detecting means for detecting defects of the repeated pattern, based on the light intensity of the specular reflection light outputted from the light receiving means. The setting means sets the angle formed by the direction on the surface of the incidence plane of the linear polarization and the repeating direction of the repeated pattern so that a difference between the intensity of light from a normal portion on the surface and the light intensity of light from a defective portion on the surface is at maximum.

11 Claims, 11 Drawing Sheets

SURFACE INSPECTING APPARATUS

TECHNICAL FIELD

The present invention relates to a surface inspecting apparatus which inspects a defect of a repetitive pattern formed in a surface of a specimen.

BACKGROUND ART

A defect of a repetitive pattern (a line-and-space pattern such as an interconnection pattern) formed in a surface of a semiconductor wafer or a liquid crystal display substrate (collectively referred to as "substrate") is inspected in a process of producing a semiconductor circuit element or a liquid crystal display element. In automatic surface inspecting apparatuses, the substrate is placed on a tiltable stage, the surface of the substrate is irradiated with testing illumination light (non-polarized light), an image of the substrate is captured based on diffracted light (for example, first-order diffracted light) generated from the repetitive pattern on the substrate, and a defective point of the repetitive pattern is identified based on a contrast of the image. Additionally, in conventional surface inspecting apparatuses, a defect of a repetitive pattern having a different repetitive pitch on the substrate can be inspected by adjusting the tilt of the stage.

Patent Document 1: Japanese Patent Publication Laid-Open No. 10-232122

However, in conventional surface inspecting apparatuses, when the repetitive pitch of the repetitive pattern is smaller than a given value (=(order of diffraction)×(wavelength of illumination light)/2), diffracted lights are not generated in principle from the repetitive pattern, and defects cannot be inspected. In the case where the repetitive pitch is brought close to the given value, due to restriction of a mechanical layout of an illumination system or a light acceptance system in the apparatuses, defect inspection can hardly be realized by diffracted lights.

In order to meet the finer repetitive pitch (that is, the finer line and space of the interconnection pattern or the like), it is thought that a wavelength of the illumination light is shortened to decrease the given value. However, a type of a light source is limited, and the light source becomes large and expensive. Furthermore, disadvantageously materials of optical elements constituting the illumination system or light acceptance system are limited to expensive ones.

An object of the present invention is to provide a surface inspecting apparatus which can surely meet a finer repetitive pitch without shortening the wavelength of the illumination light.

DISCLOSURE OF THE INVENTION

In accordance with an aspect of the present invention, a surface inspecting apparatus includes illumination means for illuminating a repetitive pattern formed in a surface of a specimen with linearly polarized light; setting means for setting an angle at a predetermined value except for zero, the angle being formed between a direction in the surface of an incident plane of the linearly polarized light and a repetitive direction of the repetitive pattern; extraction means for extracting a polarization component perpendicular to a vibration plane of the linearly polarized light from light generated in a specular reflection direction from the repetitive pattern; light acceptance means for accepting the light extracted by the extraction means and supplying light intensity of the specular reflection light; and detection means for detecting a defect of the repetitive pattern based on the light intensity of the specular reflection light supplied from the light acceptance means, wherein the setting means sets the angle formed between the direction in the surface of the incident plane of the linearly polarized light and the repetitive direction of the repetitive pattern such that a contrast becomes maximum between light intensity from a normal portion of the surface and light intensity from a defective portion of the surface.

Preferably the linearly polarized light includes light beams having plural different wavelengths.

Preferably the surface inspecting apparatus includes intensity adjusting means for adjusting an intensity distribution of the linearly polarized light including the light beams having the plural different wavelengths according to sensitivity of the detection means.

Preferably the surface inspecting apparatus includes wavelength selecting means for selecting the plural different wavelengths according to a difference between light intensity of a normal portion of the surface and light intensity of a defective portion of the surface, generated in each wavelength, and light intensity of light from the specimen of each wavelength.

Preferably the illumination means includes wavelength selecting means for changing a wavelength of the linearly polarized light, the light intensity of the specular reflection light is obtained while a wavelength of the linearly polarized light emitted from the illumination means is changed, and the defect of the repetitive pattern is detected based on light intensity obtained by combining the light intensity of the specular reflection light of each the wavelength.

Preferably a combination ratio of light intensity obtained in each wavelength is changed according to sensitivity of the detection means.

Preferably the combination ratio of the light intensity obtained in each wavelength is changed according to a difference between light intensity of a normal portion of the surface and light intensity of a defective portion of the surface, generated in each wavelength, and light intensity of light from the specimen of each wavelength.

Preferably an angle $\phi$ formed between the direction in the surface of the incident plane of the linearly polarized light and the repetitive direction of the repetitive pattern is set so as to satisfy the following equation:

$$\phi = 22.5° + 45 \times N° \text{ (N is an integer of one of 0 to 6)}$$

Preferably the surface inspecting apparatus includes first rotary means for relatively rotating the illumination means and the light acceptance means about an axis orthogonal to the surface.

Preferably the surface inspecting apparatus includes second rotary means for rotating the specimen about an axis, the axis being orthogonal to the incident plane and included in the surface.

Preferably the surface inspecting apparatus includes second rotary means for rotating at least two of the illumination means, the light acceptance means, and the specimen about an axis, the axis being orthogonal to the incident plane and included in the surface.

The surface inspecting apparatus according to the present invention can surely meet a finer repetitive pitch without shortening the wavelength of the illumination light.

BEST MODES FOR CARRYING OUT THE PRESENT INVENTION

Embodiments of the present invention will be described in detail with reference to the drawings.

First Embodiment

Figure 1:
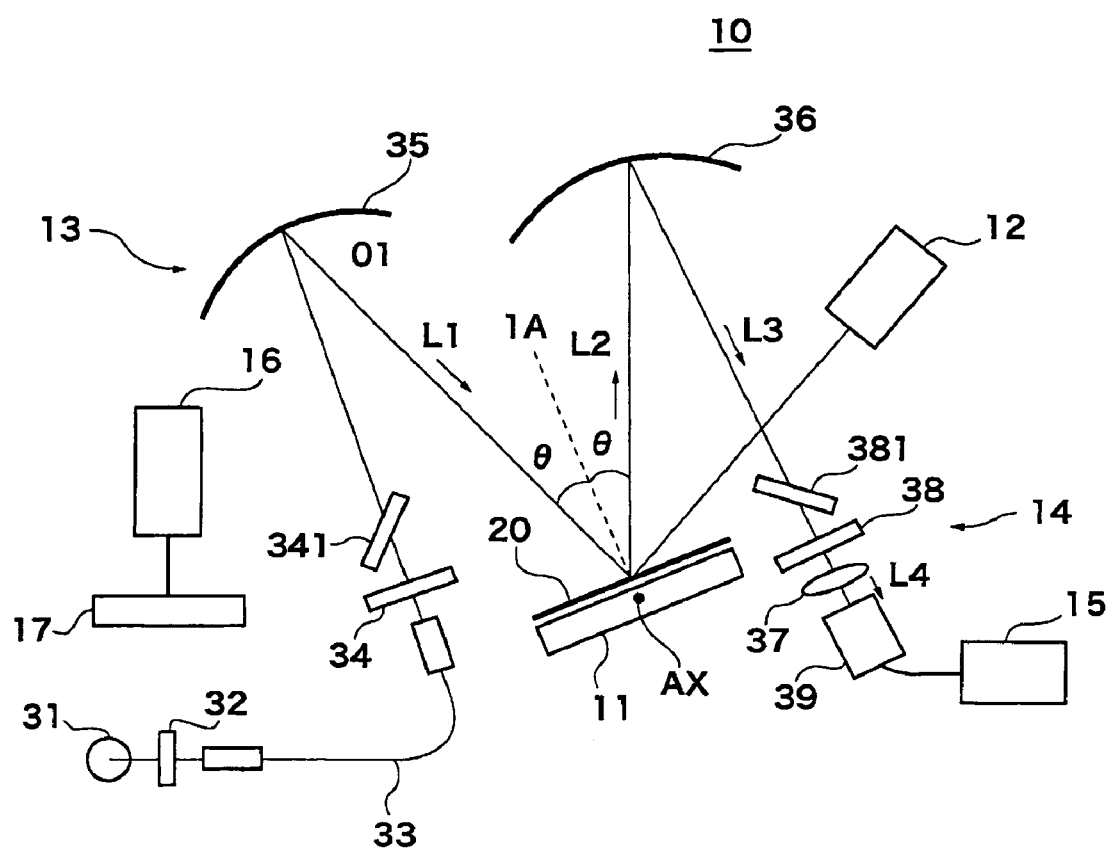
FIG. 1 is a view showing an entire configuration of a surface inspecting apparatus 10 according to a first embodiment of the present invention.

As shown in FIG. 1, a surface inspecting apparatus 10 according to a first embodiment of the present invention includes a stage 11 which supports a specimen 20, a pattern alignment system 12, an illumination system 13, a light acceptance system 14, an image processing device 15, an alignment system 16, and a conveyance stage 17.

Figure 2:
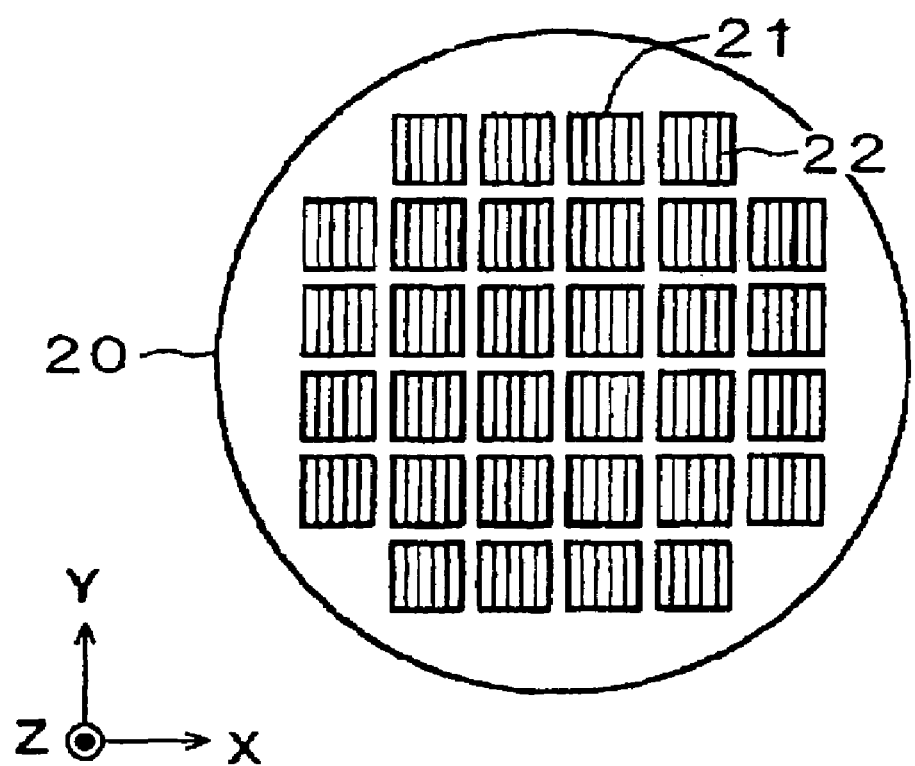
FIG. 2 shows an appearance of a surface of a specimen 20.
Figure 3:
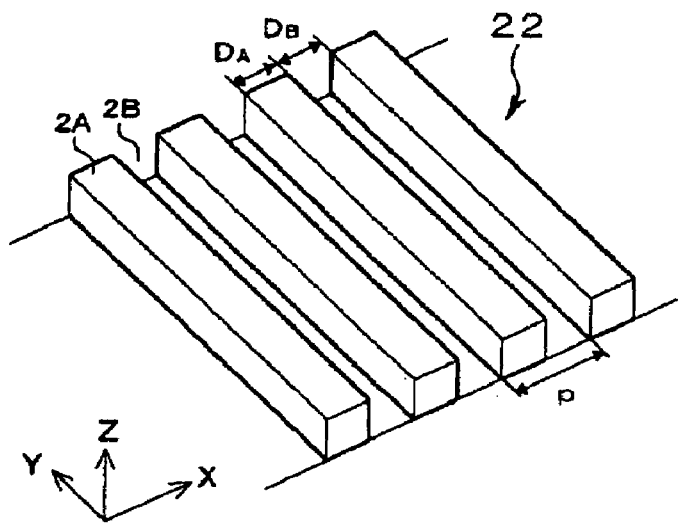
FIG. 3 is a perspective view explaining pits and projections of a repetitive pattern 22.

Examples of the specimen 20 include a semiconductor wafer and a liquid crystal display glass substrate. As shown in FIG. 2, plural shot areas 21 are arrayed in a surface (resist layer) of the specimen 20, and a repetitive pattern 22 to be inspected is formed in each shot area 21. The repetitive pattern 22 is a line-and-space pattern of an interconnection pattern or the like. As shown in FIG. 3, plural line portions 2A are arrayed at a predetermined pitch p in a lateral direction (X-direction) thereof. A space portion 2B is formed between line portions 2A adjacent to each other. The array direction (X-direction) of the line portion 2A is referred to as "repetitive direction of repetitive pattern 22".

The surface inspecting apparatus 10 of the first embodiment is an apparatus which automatically inspects a defect of the repetitive pattern 22 formed in the surface of the specimen 20 in the process of producing the semiconductor circuit element or the liquid crystal display element. The specimen 20 in which exposure and development are already performed to the surface (resist layer) is conveyed to the surface inspecting apparatus 10 from a cassette or a development apparatus by a conveyance system (not shown), and the specimen 20 is attached to the alignment stage 17 by suction.

An outer edge portion of the specimen 20 is illuminated with the alignment system 16 while the specimen 20 is rotated by the alignment stage 17, a position in a rotary direction of an outer shape reference (for example, notch) provided in the outer edge portion is detected to stop the alignment stage 17 at a predetermined position. Then, the specimen 20 is conveyed to the stage 11 by the conveyance system (not shown), and the specimen 20 is attached to the stage 11 by suction.

The defect of the repetitive pattern 22 shall mean a change in structure (that is, duty ratio or sectional shape) of the repetitive pattern 22, and the defect of the repetitive pattern 22 corresponds to a change in line width $D_A$ of the line portion 2A shown in FIG. 3 (or a change in line width $D_B$ of the space portion 2B). The pitch p is not changed even if the line widths $D_A$ and $D_B$ are changed. A defect is caused by a shift of exposure focus in forming the repetitive pattern 22, and the defect appears in each shot area 21 of the specimen 20. The stage 11 has both a rotary mechanism and a tilt mechanism, and the stage 11 rotates and tilts the specimen 20 thereon.

The stage 11 firmly retains the specimen 20 by, for example, vacuum suction while the specimen 20 is placed on a top surface thereof. A mechanism which rotates the specimen 20 about an axis orthogonal to the surface of the specimen 20 (for example, a normal 1A in the center of the surface) is also provided in the stage 11. The rotary mechanism can rotate a repetitive direction (X-direction of FIGS. 2 and 3) of the repetitive pattern 22 of the specimen 20 within the surface of the specimen 20.

A mechanism which tilts the specimen 20 about an axis AX of FIG. 1 is also provided in the stage 11. The axis AX is orthogonal to an incident plane of illumination light emitted from the illumination system 13, and the axis AX substantially passes through the center of the specimen 20 in the surface of the specimen 20. The tilt mechanism can tilt the specimen 20 at a predetermined angle in inspecting the specimen 20.

Figure 20:
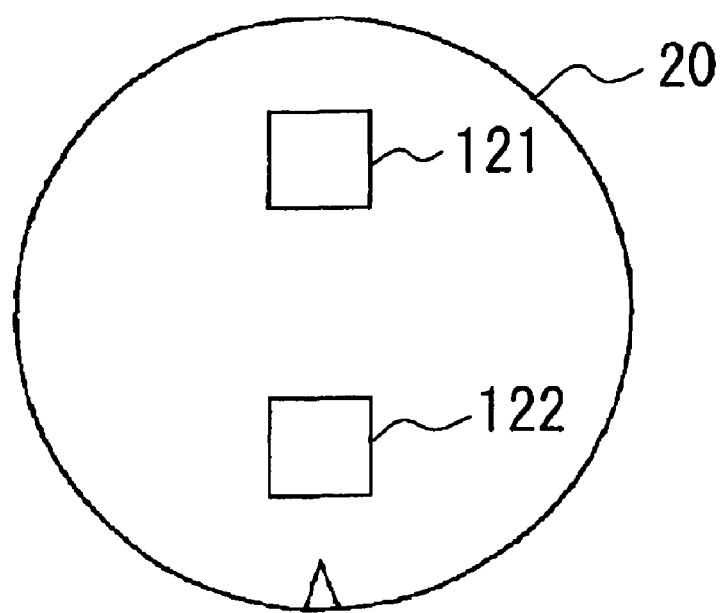
FIG. 20 is a view showing a visual field area of a pattern alignment system.

After the specimen 20 is attached to the stage 11 by suction, the pattern alignment system 12 finely adjusts the alignment in the rotary direction of the specimen 20. The pattern alignment system 12 has two imaging systems (not shown), and the imaging systems respectively take images of areas 121 and 122 on the specimen 20 as shown in FIG. 20. A rotational amount of pattern is obtained by performing image processing to the two images taken by the imaging systems. The adjustment is performed by the rotation of the stage 11 such that the rotational amount of pattern falls within a threshold.

In taking an image, the illumination system 13 illuminates the specimen 20. The pattern alignment system 12 is disposed such that specular reflection light is incident from the specimen 20 while the stage is kept level. After the pattern alignment, as shown in FIG. 1, the stage 11 tilts the specimen 20 such that the specular reflection light is incident to the light acceptance system 14 when the illumination system 13 illuminates the specimen 20.

The illumination system 13 is an eccentric optical system including a light source 31, a wavelength-selective filter 32, a lightguide fiber 33, a polarizing filter 34, a corrector plate 341, and a concave reflector 35. The illumination system 13 illuminates the repetitive pattern 22 of the specimen 20 on the stage 11 with linearly polarized light L1. The linearly polarized light L1 is illumination light for the repetitive pattern 22. The whole of the surface of the specimen 20 is illuminated with the linearly polarized light L1. The polarizing filter 34 and the corrector plate 341 can be inserted and retracted into and from an optical path by an insertion and retraction mechanism (not shown).

Figure 4:
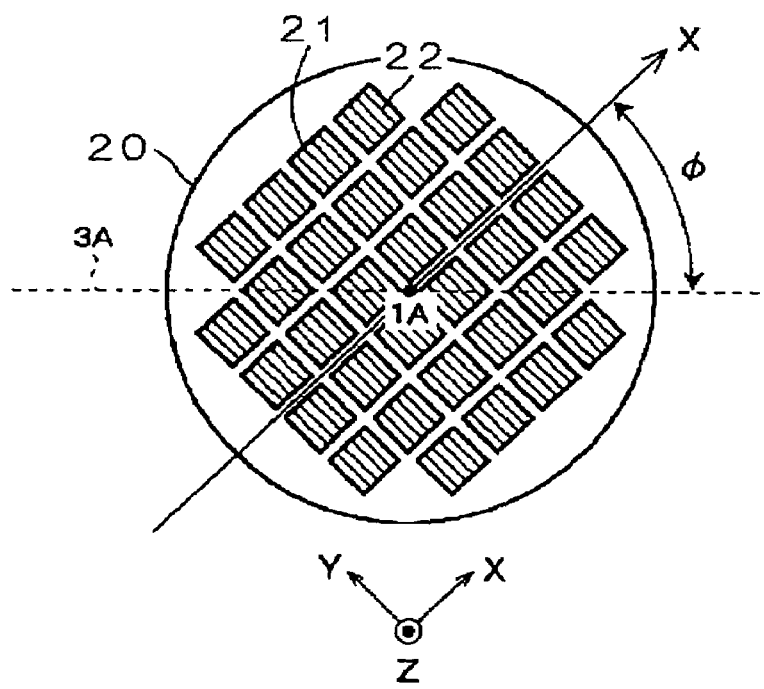
FIG. 4 is a view explaining an inclination state between an incident plane (3A) of illumination light L1 and a repetitive direction (X-direction) of the repetitive pattern 22.

A traveling direction of the linearly polarized light L1 (direction of a principal ray of the linearly polarized light L1 reaching an arbitrary point on the surface of the specimen 20) is substantially parallel to an optical axis O1 of the concave reflector 35. The optical axis O1 passes through the center of the stage 11, and the optical axis O1 is inclined by a predetermined angle θ with respect to the normal 1A of the stage 11. A plane, which includes the traveling direction of the linearly polarized light L1 and is parallel to the normal 1A of the stage 11, is the incident plane of the linearly polarized light L1. An incident plane 3A of FIG. 4 is the incident plane in the center of the specimen 20.

Figure 5:
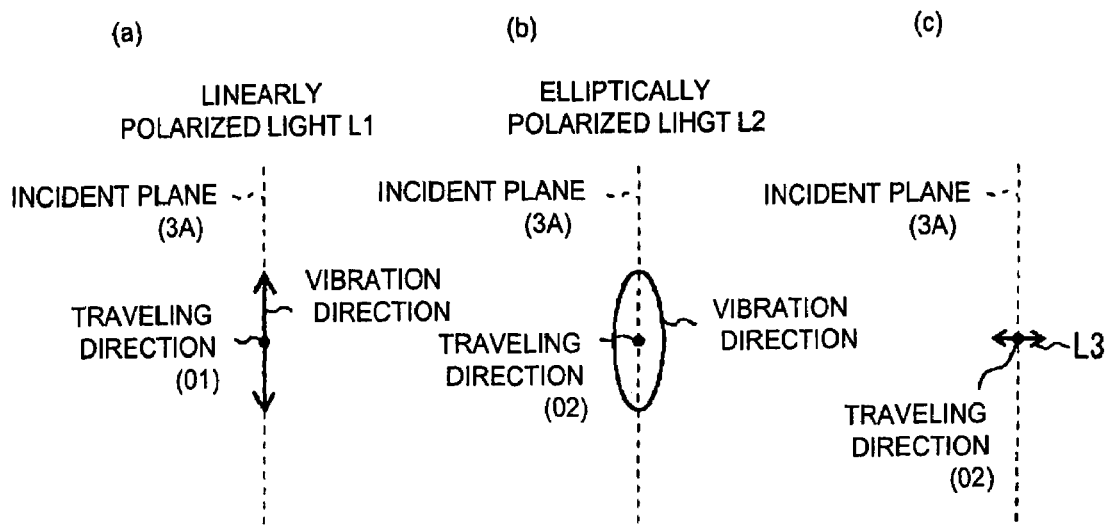
FIG. 5 is a view explaining vibration directions of linearly polarized light L1 and elliptically polarized light L2.

In the first embodiment, the linearly polarized light L1 is p-polarization. That is, as shown in FIG. 5(a), a plane (vibration plane of the linearly polarized light L1 including the traveling direction of the linearly polarized light L1 and a vibration direction of an electric (or magnetic) vector is included in the incident plane (3A) of the linearly polarized light L1. In FIG. 1, the linearly polarized light L1 is the polarized light vibrated in a paper sheet plane. The vibration plane of the linearly polarized light L1 is defined by a transmission axis of the polarizing filter 34 disposed in front of the concave reflector 35.

A discharge light source such as a metal halide lamp and a mercury lamp is used as the light source 31 of the illumination system 13. The wavelength-selective filter 32 selectively transmits an emission line spectrum having a predetermined wavelength in the light emitted from the light source 31. The lightguide fiber 33 transmits the light from the wavelength-selective filter 32. The polarizing filter 34 is disposed near an outgoing end of the lightguide fiber 33, the transmission axis of the polarizing filter 34 is set toward a predetermined orientation, and the polarizing filter 34 converts the light from the lightguide fiber 33 into the linearly polarized light according to the transmission axis. The concave reflector 35 is a reflector whose reflecting surface is an inner spherical surface, and the concave reflector 35 is disposed such that a front focal point of the concave reflector 35 is substantially matched with the outgoing end of the lightguide fiber 33 while a back focal point of the concave reflector 35 is substantially matched with the surface of the specimen 20. The concave reflector 35 guides the light from the polarizing filter 34 to the surface of the specimen 20. The illumination system 13 is an optical system which is telecentric with respect to the side of the specimen 20. The corrector plate 341 will be described later.

In the illumination system 13, the light emitted from the light source 31 travels through the wavelength-selective filter 32, lightguide fiber 33, polarizing filter 34, and concave reflector 35 and is formed into the p-polarization linearly polarized light L1 (FIG. 5(a)). Then, the p-polarization linearly polarized light L1 is incident to the whole of the surface of the specimen 20. The incident angles of the linearly polarized light L1 at points on the specimen 20 are equal to one another, and the incident angle corresponds to an angle θ formed between the optical axis O1 and the normal 1A.

In the first embodiment, because the linearly polarized light L1 incident to the specimen 20 is the p-polarization (FIG. 5(a)), an angle formed between the direction (V-direction of FIG. 6) of the vibration plane of the linearly polarized light L1 in the surface of the specimen 20 and the repetitive direction (X-direction) of the repetitive pattern 22 is set at an angle φ, when the repetitive direction (X-direction) of the repetitive pattern 22 of the specimen 20 is set at the angle φ with respect to the incident plane (3A) of the linearly polarized light L1 as shown in FIG. 4. The angle φ is set to 22.5 degrees or 67.5 degrees.

In other words, the linearly polarized light L1 incident to the repetitive pattern 22 obliquely traverses the repetitive pattern 22 such that the vibration plane direction (V-direction of FIG. 6) in the surface of the specimen 20 is inclined by the angle φ (22.5 degrees or 67.5 degrees) with respect to the repetitive direction (X-direction) of the repetitive pattern 22.

The angle state between the linearly polarized light L1 and the repetitive pattern 22 is kept constant over the whole surface of the specimen 20. The angle state between the linearly polarized light L1 and the repetitive pattern 22 is not changed even if the 22.5 degrees are replaced with one of 115.5 degrees, 205.5 degrees, and 295.5 degrees, and even if the 67.5 degrees are replaced with one of 157.5 degrees, 247.5 degrees, and 337.5 degrees.

The angle setting is performed using the rotary mechanism of the stage 11. For example, a pulse motor is used as the rotary mechanism, and the angle (hereinafter referred to as "rotary angle φ") can be set by delivering the number of pulses corresponding to a predetermined rotary angle.

When the repetitive pattern 22 is illuminated with the linearly polarized light L1, elliptically polarized light L2 is generated in a specular reflection direction from the repetitive pattern 22 (FIGS. 1 and 5(b)). In this case, the traveling direction of the elliptically polarized light L2 is matched with the specular reflection direction. The specular reflection direction shall mean a direction which is included in the incident plane (3A) of the linearly polarized light L1 and inclined by an angle θ (equal to the incident angle θ of the linearly polarized light L1 with respect to the normal 1A of the stage 11. As described above, because the pitch P of the repetitive pattern 22 is sufficiently smaller than the wavelength of the illumination light, a diffracted light is not generated from the repetitive pattern 22.

The reason why the linearly polarized light L1 is formed into elliptical polarization by the repetitive pattern 22 to generate the elliptically polarized light L2 by the repetitive pattern 22 is described in detail in WO2005/040776 filed by the applicant, and therefore the description will be omitted.

Figure 6:
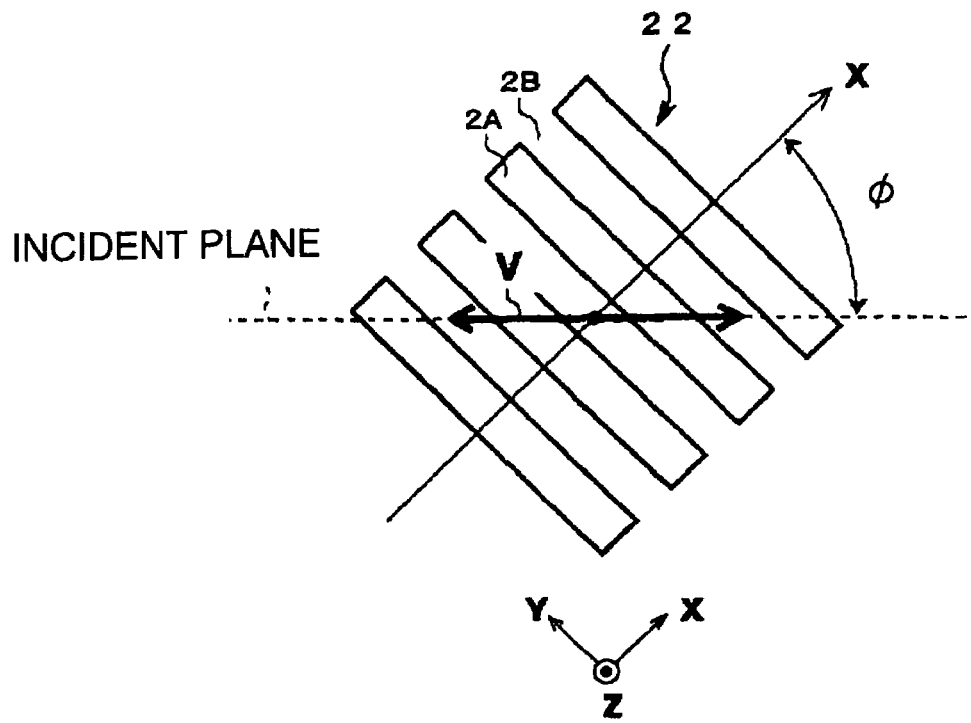
FIG. 6 is a view explaining an inclination state between a vibration-plane direction (V-direction) of the linearly polarized light L1 and the repetitive direction (X-direction) of the repetitive pattern 22.

The reason why the angle φ formed between the vibration plane direction (V-direction) of FIG. 6 and the repetitive direction (X-direction) is set to 22.5 degrees or 67.5 degrees is that sensitivity of the defect inspection of the repetitive pattern 22 is enhanced. The reason will be described below in detail.

In WO2005/040776, the inventors described that the angle φ formed between the vibration plane direction (V-direction)

of FIG. 6 and the repetitive direction (X-direction) should desirably be set to 45 degrees. According to the description this is attributed to the fact that a deterioration rate from the luminance value of the image reflected from the normal pattern to the luminance value of the image reflected from the defective pattern (luminance value of image reflected from defective pattern/luminance value of image reflected from normal pattern) is kept constant irrespective of the angle $\phi$, that is, a deterioration amount (difference in luminance value) from the luminance value of the image reflected from the normal pattern to the luminance value of the image reflected from the defective pattern is decreased as the inclination angle $\phi$ deviates from the 45 degrees.

In the relationship between the luminance value of the normal repetitive pattern and the rotary angle $\phi$, the luminance value becomes the maximum when the rotary angle $\phi$ is set to 45 degrees (because the reason is described in detail in WO2005/040776, the description is omitted).

However, the inventors have found that a ratio of (luminance value of image reflected from defective pattern (measured value)) and (luminance value of image reflected from normal pattern (measured value)) depends on the angle $\phi$, and the evaluation can be made with the highest sensitivity when the defect inspection is performed on the condition of the angle $\phi$ at which a contrast becomes the maximum.

Figure 7:
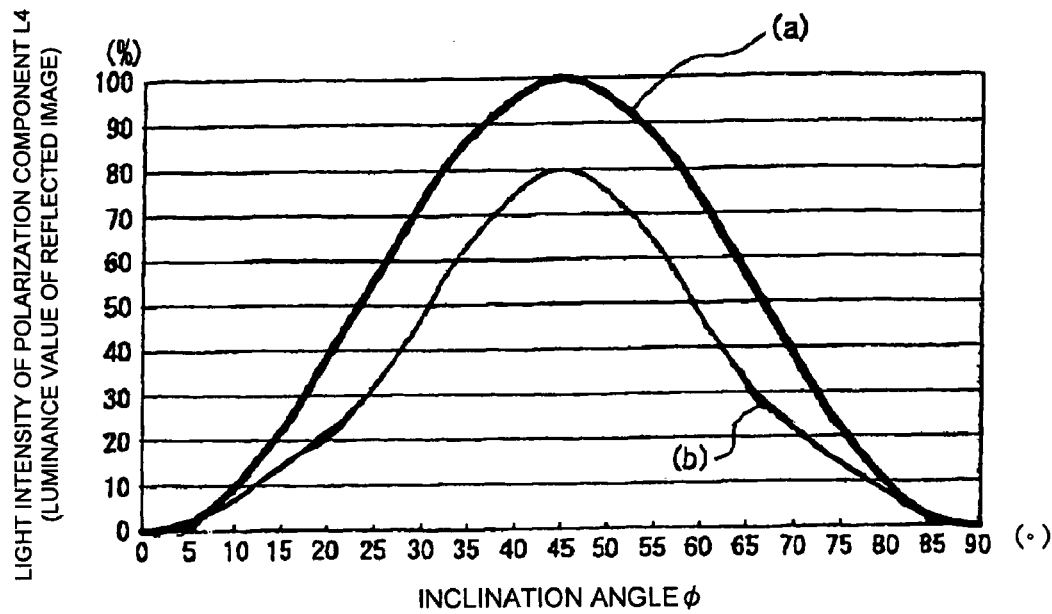
FIG. 7 is a view showing a relationship (a) between a luminance value (light intensity of a polarization component L4) of an image reflected from a normal pattern and an angle φ formed by the vibration plane and the repetitive direction and a relationship (b) between a luminance value (light intensity of a polarization component L4) of an image reflected from a defective pattern and the angle φ formed by the vibration plane and the repetitive direction.
Figure 8:
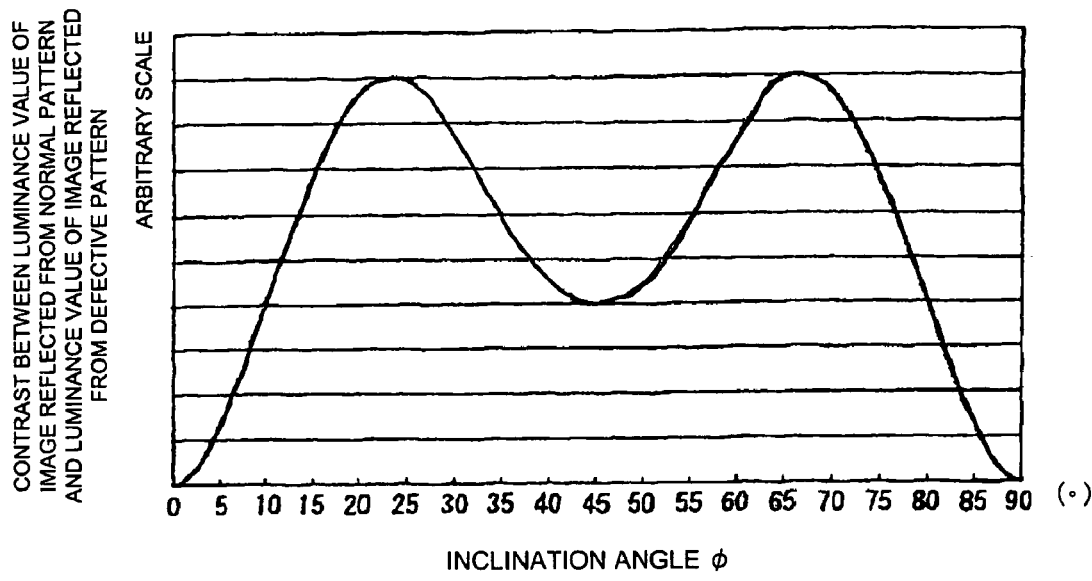
FIG. 8 is a view showing a contrast between the luminance value of the image reflected from the normal pattern and the luminance value of the image reflected from the defective pattern.

FIG. 7 shows a relationship (a) between the luminance value (light intensity of the polarization component L4) of the image reflected from the normal pattern and the angle $\phi$ formed by the vibration plane of the linearly polarized light and the pattern and a relationship (b) between the luminance value (light intensity of the polarization component L4) of the image reflected from the defective pattern and the angle $\phi$ formed by the vibration plane of the linearly polarized light and the pattern. FIG. 8 shows the contrast between the luminance value of the image reflected from the normal pattern and the luminance value of the image reflected from the defective pattern. As can be seen from FIG. 8, the contrast becomes the maximum when the angle $\phi$ is set to 22.5 degrees and 67.5 degrees.

As used herein, the contrast shall mean an absolute value (1-[(luminance value of image reflected from defective pattern (measured value))/(luminance value of image reflected from normal pattern (measured value))]). The contrast of 1 means (luminance value of image reflected from normal pattern (measured value))/(luminance value of image reflected from normal pattern (measured value)). That is, the luminance value of the image reflected from the normal pattern (measured value) is normalized as 1.

Examples will be described below.

(1) At the angle $\phi$ of 45 degrees,
  in the case of luminance value of image reflected from normal pattern=100 and luminance value of image reflected from defective pattern=80,
  the contrast is given as follows:

$$[1(=100/100)-(80/100)]=0.2$$

(2) At the angle $\phi$ of 35 degrees,
  in the case of luminance value of image reflected from normal pattern=85 and luminance value of image reflected from defective pattern=62.5,
  the contrast is given as follows:

$$[1(=85/85)-(62.5/85)]=0.26$$

(3) At the angle $\phi$ of 30 degrees,
  in the case of luminance value of image reflected from normal pattern=70 and luminance value of image reflected from defective pattern=45,
  the contrast is given as follows:

$$[1(=70/70)-(45/70)]=0.36$$

(4) At the angle $\phi$ of 22.5 degrees,
  in the case of luminance value of image reflected from normal pattern=45 and luminance value of image reflected from defective pattern=25,
  the contrast is given as follows:

$$[1(=45/45)-(25/45)]=0.44$$

(5) At the angle $\phi$ of 15 degrees,
  in the case of luminance value of image reflected from normal pattern=20 and luminance value of image reflected from defective pattern=15,
  the contrast is given as follows:

$$[1(=20/20)-(15/20)]=0.25$$

(6) At the angle $\phi$ of 10 degrees,
  in the case of luminance value of image reflected from normal pattern=10 and luminance value of image reflected from defective pattern=8,
  the contrast is given as follows:

$$[1(=10/10)-(8/10)]=0.2$$

Thus, the contrast at the angle $\phi$ of 22.5 degrees is larger than the contrasts at other angles. The contrast at the angle $\phi$ of 67.5 degrees becomes the maximum because a light intensity distribution is symmetric in relation to the angle $\phi$ of 45 degrees.

Alternatively, the contrast is defined as follows.

After an illumination light quantity has been adjusted or an image taking time has been adjusted in each angle $\phi$ such that the luminance value (measured value) of the image reflected from the normal pattern in each angle $\phi$ becomes a predetermined luminance value (normal pattern specification (for example, 100)), the luminance value of the image reflected from the normal pattern is obtained, and the luminance value of the image reflected from the defective pattern (defective pattern specification value) is obtained in each angle $\phi$ using the illumination light quantity or the image taking time.

An absolute value of a difference between the normal pattern specification value and the defective pattern specification value in each angle $\phi$ may be defined as the contrast.

The light acceptance system 14 will be described below. As shown in FIG. 1, the light acceptance system 14 is an eccentric optical system including a concave reflector 36, an image-formation lens 37, a polarizing filter 38, a corrector plate 381, and an imaging device 39. The polarizing filter 38 and the corrector plate 381 can be inserted and retracted into and from the optical path by an insertion and retraction mechanism (not shown).

The concave reflector 36 is a reflector similar to the concave reflector 35 of the illumination system 13, and the concave reflector 36 is disposed such that an optical axis O2 of the concave reflector 36 passes through the center of the stage 11 and is inclined by the angle $\theta$ with respect to the normal 1A of the stage 11 (in other words, the stage 11 is tilted such that both the optical axis O1 of the illumination system 13 and the optical axis O2 of the light acceptance system 14 are set to angle $\theta$ with respect to the normal 1A of the stage 11). Accordingly, the elliptically polarized light L2 from the repetitive pattern 22 travels along the optical axis O2 of the concave reflector 36. The concave reflector 36 reflects the elliptically polarized light L2 toward the image-formation lens 37, and in cooperation with the image-formation lens 37 the concave reflector 36 collects the elliptically polarized light L2 in an imaging plane of the imaging device 39. A plane formed by the optical axes before and after reflection of the elliptically polarized light L2 on the concave reflector 36 is orthogonal to the incident plane (the plane is parallel to the incident plane in the drawing).

However, the polarizing filter 38 is disposed between the image-formation lens 37 and the concave reflector 36. An orientation of the transmission axis of the polarizing filter 38 is set so as to be orthogonal to the transmission axis of the polarizing filter 34 of the illumination system 13 (crossed-Nicol state). Accordingly, only the polarization component L4 (FIG. 1) corresponding to the polarization component L3 of FIG. 5(c) of the elliptically polarized light L2 can be extracted by the polarizing filter 38 and guided to the imaging device 39.

In other words, only an s-polarization component is extracted in the elliptically polarized light L2 reflected from the specimen 20. The s-polarization shall mean linearly polarized light whose vibration plane is perpendicular to the incident plane, and the s-polarization is vibrated in a direction perpendicular to the paper sheet plane of FIG. 1. The image reflected from the specimen 20 is formed in the imaging plane of the imaging device 39 by the polarization component L4 (s-polarization component). The corrector plate 381 will be described later.

Figure 9:
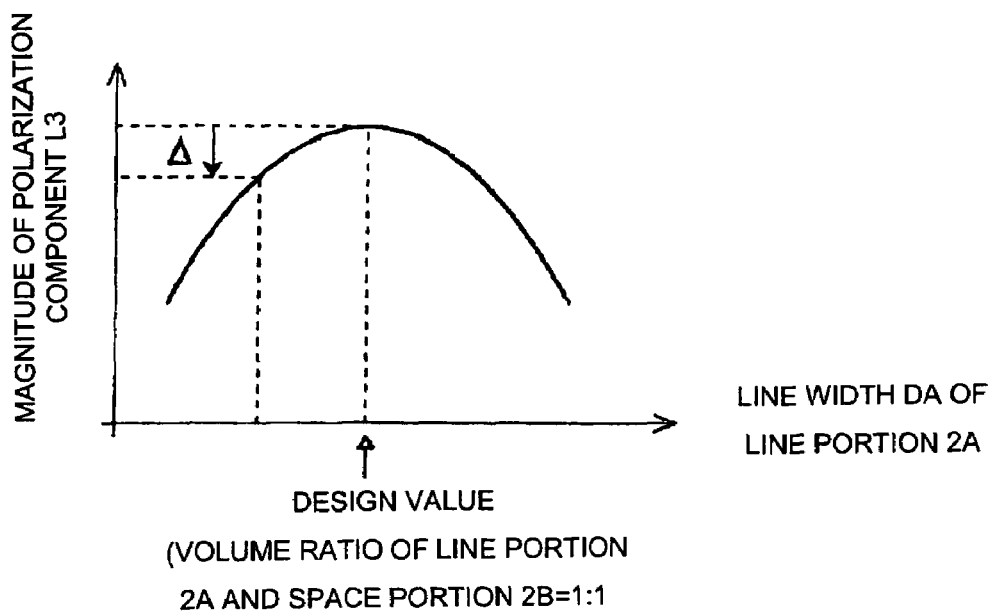
FIG. 9 is a view explaining a relationship between magnitude of a polarization component L3 and a line width $D_A$ of a line portion 2A in the repetitive pattern 22.

For example, a CCD imaging device is used as the imaging device 39. The imaging device 39 performs optoelectric conversion of the image which is reflected from the specimen 20 and formed in the imaging plane, and the imaging device 39 supplies an image signal to the image processing device 15. The contrast of the image reflected from the specimen 20 is substantially proportional to light intensity of the polarization component L4 (magnitude of the polarization component L3 of FIG. 5(c)), and the contrast is changed according to a shape (volume ratio of the line portion 2A and space portion 2B) of the repetitive pattern 22 (see FIG. 9). The image reflected from the specimen 20 becomes brightest in the case where the repetitive pattern 22 is an ideal shape (volume ratio is 1:1). The contrast of the image reflected from the specimen 20 appears in each shot area.

The image processing device 15 captures the image reflected from the specimen 20 based on the image signal supplied from the imaging device 39. For the purpose of comparison, the image processing device 15 has previously obtained in a storage an image reflected from an acceptable wafer, which is obtained when the rotary angle φ is set to 22.5 degrees or 67.5 degrees. The acceptable wafer shall mean a wafer in which the repetitive pattern 22 is formed over the surface with the ideal shape (volume ratio is 1:1). Further, when capturing the image reflected from the specimen 20, the image processing device 15 compares luminance information on the captured image to luminance information on the image reflected from the acceptable wafer.

Then, a defect (a change in volume ratio between the line portion 2A and the space portion 2B) of the repetitive pattern 22 is detected based on the contrast between the luminance value of the image reflected from the acceptable wafer and the luminance value of the image reflected from the specimen 20. For example, when the contrast of the luminance value is larger than a predetermined threshold (allowance), it is determined that the specimen 20 is "defective". When the contrast is smaller than the threshold, it is determined that the specimen 20 is "normal".

In the image processing device 15, a configuration in which shot area array data of the wafer and a luminance value threshold are previously stored may be adopted instead of the configuration in which the image reflected from the acceptable wafer has previously been obtained in a storage as described above. At this point, the luminance value is obtained in each shot area because the position of each shot area is learned in the captured image reflected from the wafer based on the shot area array data. The defect of the pattern is detected by comparing the obtained luminance value to the stored threshold. When the luminance value is smaller than the threshold, it is determined that the shot area is defective.

The repetitive pattern has the same arrangement in each shot area 21 of the specimen 20, an acceptable shot area 21 is specified, and a defect may be detected based on the luminance value of the acceptable shot area. A luminance value of the image of the specimen 20 may be compared to a luminance value of an image of a critical sample. A reference of the luminance value is obtained by a simulation, and a defect of the repetitive pattern 22 may be detected by the comparison with the obtained reference value. In the case where an acceptable wafer is not used, advantageously it is not necessary to prepare a dedicated wafer in which a defect does not exist over the whole surface thereof.

Both the image at the angle of 22.5 degrees and the image at the angle of 67.5 degrees are taken and inspected, and the determination of presence or absence of a defect may finally be made by operating AND or OR.

Thus, in the surface inspecting apparatus 10 of the first embodiment, the repetitive pattern 22 is illuminated with the linearly polarized light L1 while the vibration plane direction (V-direction) of FIG. 6 is inclined with respect to the repetitive direction (X-direction) of the repetitive pattern 22, and a defect of the repetitive pattern 22 is detected based on the light intensity of the polarization component L4 (magnitude of polarization component L3 of FIG. 5(c)) in the elliptically polarized light L2 generated in the specular reflection direction. Therefore, even if the pitch P of the repetitive pattern 22 is sufficiently smaller than the wavelength of the illumination light, the defect inspection can surely be performed. That is, the surface inspecting apparatus 10 of the first embodiment can surely meet the finer repetitive pitch, even if the wavelength of the linearly polarized light L1 which is of the illumination light is not shortened.

In the surface inspecting apparatus 10 of the first embodiment, the angle φ formed between the vibration plane direction (V-direction) of FIG. 6 and the repetitive direction (X-direction) is set to 22.5 degrees or 67.5 degrees, so that the contrast between the luminance value of the image reflected from the acceptable wafer and the luminance value of the image reflected from the specimen 20 can be increased to perform the defect inspection of the repetitive pattern 22 with high sensitivity.

In the surface inspecting apparatus 10 of the first embodiment, a defect of the repetitive pattern 22 can be inspected not only in the case where the pitch P of the repetitive pattern 22 is sufficiently smaller than the wavelength of the illumination light, but also in the case where the pitch P of the repetitive pattern 22 is similar to or larger than the wavelength of the illumination light. That is, the defect inspection can surely be performed irrespective of the pitch P of the repetitive pattern 22. This is because how the linearly polarized light L1 is formed into the elliptically polarized light by the repetitive pattern 22 depends not on the pitch P of the repetitive pattern 22, but on the volume ratio of the line portion 2A and space portion 2B of the repetitive pattern 22.

Figure 10:
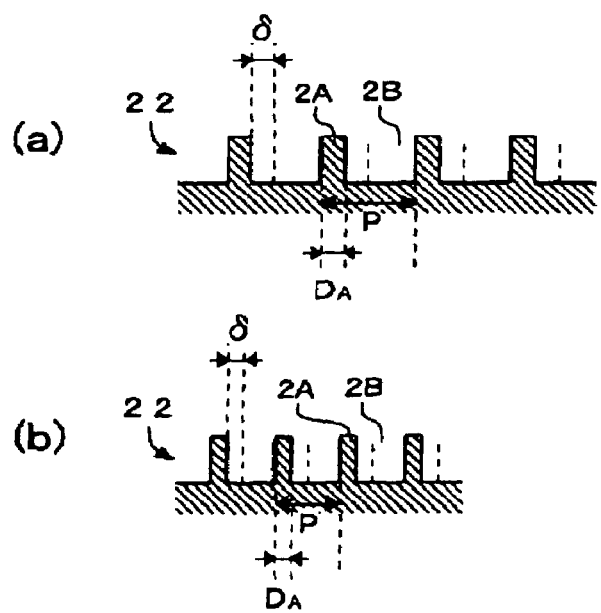
FIG. 10 is a view showing an example of repetitive patterns 22 in which a volume ratio of the line portion 2A and a space portion 2B is kept constant while a pitch P is changed.

In the surface inspecting apparatus 10 of the first embodiment, when the volume ratio of the line portion 2A and space portion 2B of the repetitive pattern 22 is kept constant, the deterioration amount (deterioration amount Δ of FIG. 9) of luminance value of the reflected image is equalized. Therefore, when a change in volume ratio is kept constant irrespective of the pitch P of the repetitive pattern 22, the detection can be performed with the same sensitivity. For example, the defect inspection can be performed with the same sensitivity, in the case where the volume ratio of the line portion 2A and the space portion 2B is kept constant while the pitch P is changed like the repetitive pattern 22 shown in FIGS. 10(a) and 10(b). As can be seen from the comparison of FIGS. 10(a) and 10(b), a finer change in shape (an amount δ of shift of the line width $D_A$ of the line portion 2A from a design value) can surely be detected as the pitch P is decreased.

Figure 11:
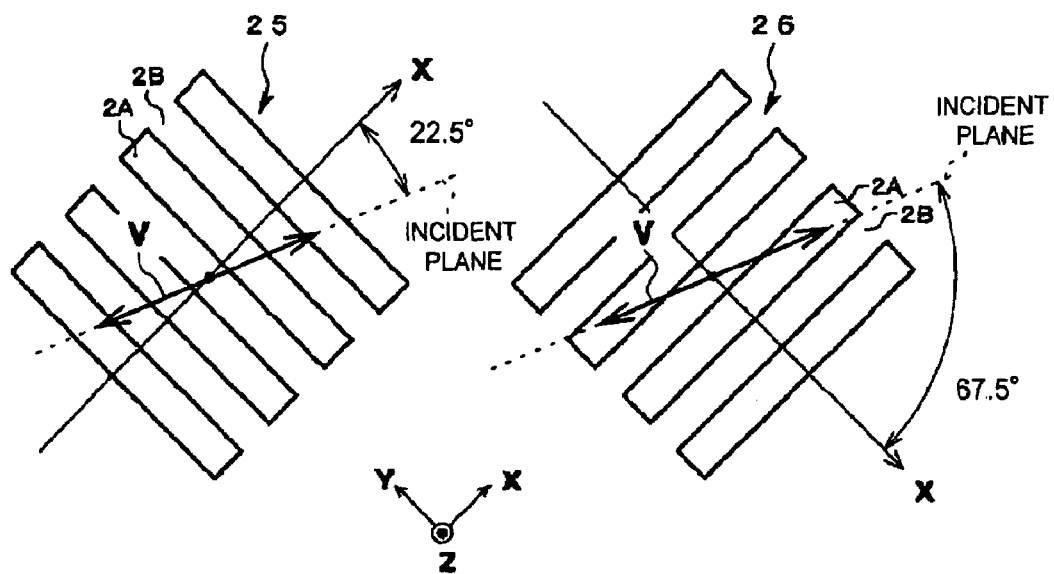
FIG. 11 is a view explaining repetitive patterns 25 and 26 which differ from each other in the repetitive direction.

In the surface inspecting apparatus 10 of the first embodiment, because the discharge light source can be used as the light source 31 of the illumination system 13, the entire configuration of the surface inspecting apparatus 10 becomes simple and inexpensive. In the surface inspecting apparatus 10 of the first embodiment, even if plural kinds of repetitive patterns having different pitches P and repetitive directions (X-directions) are formed in the surface of the specimen 20, only the image reflected from the whole surface of the specimen 20 is collectively captured to check the contrast of the luminance value at each point, which allows a defect to be simply inspected for all the repetitive patterns. The repetitive patterns having the different repetitive directions are a repetitive pattern 25 in a zero-degree direction and a repetitive pattern 26 in a 90-degree direction as shown in FIG. 11. The repetitive directions (X-direction) of the repetitive patterns 25 and 26 differ from each other by 90 degrees.

However, in each of the repetitive patterns 25 and 26, the angle formed by the repetitive direction (X-direction) and the vibration plane direction (V-direction) of the linearly polarized light L1 are set to 22.5 degrees or 67.5 degrees.

In the surface inspecting apparatus 10 of the first embodiment, defect information on asymmetry (for example, a collapse direction of the edge shape) of an edge shape of the line portion 2A in the repetitive pattern 22 can also be obtained, because the linearly polarized light L1 is obliquely incident to the surface of the specimen 20 (see FIG. 1). For this end, the repetitive direction (X-direction) of the repetitive pattern 22 of the specimen 20 is rotated by 180 degrees with the stage 11, the image reflected from the specimen 20 is captured before and after the rotation, and the difference in luminance value is checked at the same point.

Figure 12:
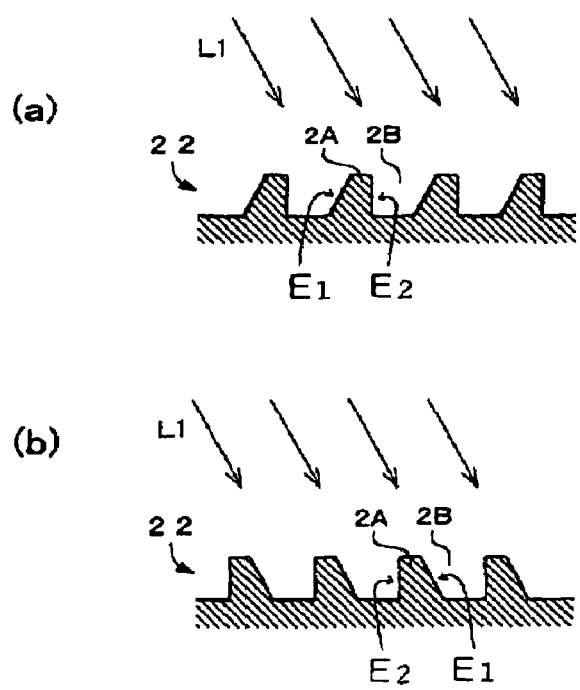
FIG. 12 is a view showing a relationship between the repetitive pattern 22 whose edge shape is asymmetric and an incident direction of the linearly polarized light L1.

FIG. 12 shows a relationship between the repetitive pattern 22 having the asymmetric edge shape and the incident direction of the linearly polarized light L1. For example, FIG. 12(a) shows the state before the repetitive direction is rotated by 180 degrees, and the illumination light is incident from side of a collapsed edge ($E_1$) in edges $E_1$ and $E_2$ of the line portion 2A. FIG. 12(b) shows the state after the repetitive direction is rotated by 180 degrees, and the illumination light is incident from side of the edge ($E_2$) which is not collapsed in the edges $E_1$ and $E_2$. The edge shapes of the edges $E_1$ and $E_2$ located in the incident direction are reflected on the luminance values of the reflected images captured in the states. In the example of FIG. 12, the case of FIG. 12(a) is larger than the case of FIG. 12(b) in the luminance value of the reflected image. Accordingly, the asymmetry of the edge shape of the line portion 2A can be learned by checking the difference in luminance value of the reflected image before and after the repetitive direction is rotated by 180 degrees. Alternatively, the defect inspection may be performed after the reflected images before and after the repetitive direction is rotated by 180 degrees have been combined.

In the case where the linearly polarized light L1 is obliquely incident to the surface of the specimen 20 (see FIG. 1, incident angle θ) in the first embodiment, strictly the elliptically polarized light L2 (FIG. 5(b)) generated from the repetitive pattern 22 is slightly rotated about the traveling direction of the elliptically polarized light L2. The polarization component L1 and the elliptically polarized light L2 are slightly rotated when reflected from the concave mirrors 35 and 36. The rotation in the reflection is not even in the reflection plane. Therefore, the orientation of the transmission axis of the polarizing filter 38 in the light acceptance system 14 should preferably be finely adjusted in consideration of the rotary angle of the polarized light.

After the fine adjustment, although an angle between the transmission axes of the two polarizing filters 34 and 38 are not correctly 90 degrees, the angle after the fine adjustment is also included in "perpendicular (or orthogonal)", and it is said that the crossed-Nicol state is established. The inspection accuracy can be improved by finely adjusting the orientation of the transmission axis of the polarizing filter 38.

With reference to the finely adjusting method, for example, an image is captured by reflecting the linearly polarized light L1 from the surface in which no repetitive pattern exists, and the orientation of the transmission axis of the polarizing filter 38 is rotated such that the luminance value of the image becomes the minimum. The corrector plates are respectively inserted between the polarizing filters 34 and 38 and the concave mirrors 35 and 36 to further perform the fine adjustment. For this purpose, in the apparatus of FIG. 1, the corrector plates 341 and 381 are inserted between the polarizing filters 34 and 38 and the concave mirrors 35 and 36, respectively. As a corrector plate, for example, a glass plane-parallel plate on a surface of which a protective film having the same refractive index as glass is coated, may be used. The corrector plate is obliquely inserted into the optical path and the inclination angle is adjusted, so that the rotation caused by the concave mirror can be corrected.

Although the linearly polarized light L1 is the p-polarization in the first embodiment, the present invention is not limited to the p-polarization. Not the p-polarization but the s-polarization may be used as the linearly polarized light L1. Therefore, as shown in FIG. 4, in the case where the repetitive direction (X-direction) of the repetitive pattern 22 in the specimen 20 is set to the angle of 22.5 degrees or 67.5 degrees with respect to the incident plane (3A) of the s-polarized light which is of the linearly polarized light L1, the angle formed between the vibration plane direction of the s-polarized light in the surface of the specimen 20 and the repetitive direction (X-direction) of the repetitive pattern 22 is also set to 22.5 degrees or 67.5 degrees. Advantageously the p-polarized light is used to obtain defect information on the edge shape of the line portion 2A in the repetitive pattern 22. Advantageously the s-polarized light efficiently obtains defect information on the surface of the specimen 20 to improve an SN ratio.

In addition to the p-polarized light and the s-polarized light, linearly polarized light whose vibration plane is arbitrarily inclined with respect to the incident plane may be used as the linearly polarized light L1. At this point, preferably the repetitive direction (X-direction) of the repetitive pattern 22 is set at an angle except for 22.5 degrees or 67.5 degrees with respect to the incident plane of the linearly polarized light L1, and the angle formed between the vibration plane direction of the linearly polarized light L1 in the surface of the specimen 20 and the repetitive direction (X-direction) of the repetitive pattern 22 should preferably be set at 22.5 degrees or 67.5 degrees.

A wavelength included in an absorption band of an anti-reflection coating (ARC) of the specimen 20 should preferably be selected as a wavelength λ of the illumination light L1. At this point, the light quantity reaching a ground is attenuated due to the absorption in the anti-reflection coating, so that the selection of the wavelength has an advantage for separation between the surface and the ground. The wavelength can be selected in such a manner that information on the wavelength λ is read from an inspection recipe to switch the wavelength-selective filters 32.

Second Embodiment

An example in which the illumination light L1 includes light beams having plural different wavelengths will be described. Examples of the plural wavelengths include discrete spectra such as plural emission line spectra and continuous spectrum such as a broad waveband. In the following description, it is assumed that the illumination light L1 includes plural emission line spectra having different wavelengths.

Figure 13:
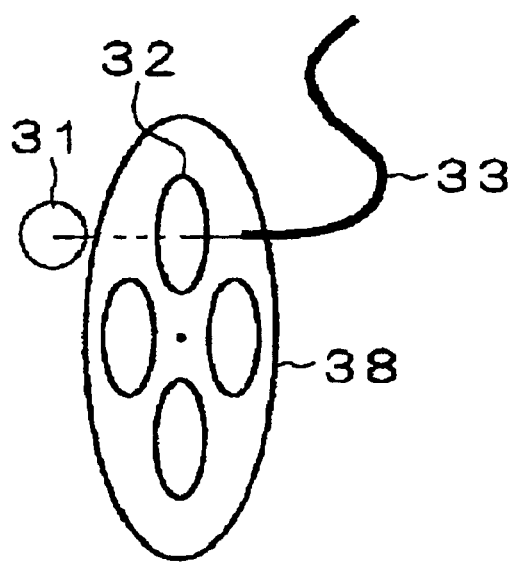
FIG. 13 is a view explaining a mechanism for switching wavelength-selective filters.

Each wavelength λ of the plural emission line spectra is appropriately selected by switching wavelength-selective filters 32, and the wavelength included in the absorption band of the anti-reflection coating of the specimen 20 is selected more preferably. With reference to the mechanism for switching wavelength-selective filters 32, for example, plural wavelength-selective filters 32 having the different transmission bands are attached to a disc-shape turret 38 as shown in FIG. 13, and the turret 38 is rotated by a drive mechanism such as a motor (not shown).

Figure 14:
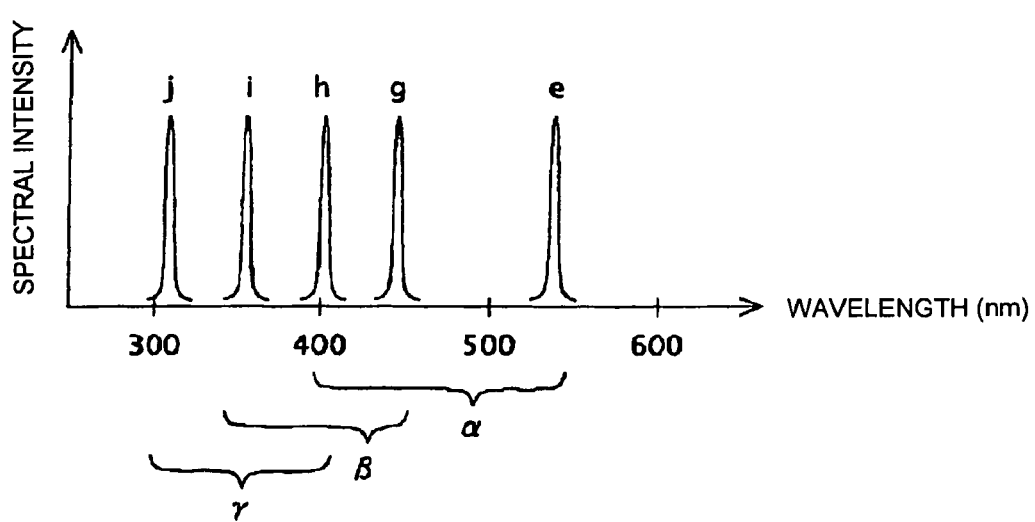
FIG. 14 is a view showing an example of emission line spectra included in light from a light source 31.

In the case where the light emitted from the light source 31 includes, for example, many emission line spectrum (such as an e line) as shown in FIG. 14, when a wavelength-selective filter 32 having the transmission band α is disposed on the optical path the wavelength-selective filter 32 having the transmission band α can selectively transmit three emission line spectra including the e line (546 nm), g line (436 nm), and h line (405 nm) to illuminate the specimen 20 with the illumination light L1. When the wavelength-selective filter 32 having the transmission band α is replaced with a wavelength-selective filter 32 having the transmission band β, the wavelength-selective filter 32 having the transmission band β can selectively transmit three emission line spectra including the g line, h line, and i line (365 nm) to illuminate the specimen 20. When the wavelength-selective filter 32 having the transmission band β is replaced with a wavelength-selective filter 32 having the transmission band γ, the wavelength-selective filter 32 having the transmission band γ can selectively transmit three emission line spectra including the h line, i line, and j line (313 nm) to illuminate the specimen 20.

In the case where the illumination light L1 includes plural emission line spectra, the elliptically polarized light L2 is generated from the specimen 20 by the emission line spectrum of each wavelength λ, the light intensity of the polarization component L4 in the elliptically polarized light L2 of each wavelength λ is combined in the imaging plane of the imaging device 39. The image signal supplied from the imaging device 37 to the image processing device 15 will be information on the light intensity after the combination of the polarization components L4 of the wavelengths λ. In this case, the image processing device 15 performs the defect inspection of the repetitive pattern 22 based on the light intensity after the combination.

In the case where unevenness of a film thickness is generated in the ground of the specimen 20, a defect of the repetitive pattern 22 in the surface is hardly inspected, if an interference fringe (contrast pattern caused by the interference in the ground) affected by the unevenness of the film thickness overlaps the image of the polarization component L4 (signal light) reflected from the surface to be inspected. In the case where the illumination light L1 is of a single wavelength, when if the interference fringe affected by the unevenness of the film thickness of the ground is generated, the interference fringe overlaps the image reflected from the surface, so that a good defect inspection cannot be performed.

However, in the surface inspecting apparatus of the present embodiment, because the illumination light L1 includes the plural emission line spectra, even if an interference fringe affected by the unevenness of the thickness of the ground is generated, the state (shape) of the interference fringe depends on each wavelength λ, and therefore the contrast pattern can be canceled by combining light intensities of the interference fringes each of which corresponds to wavelength λ. That is, an influence of the interference fringe affected by the unevenness of the film thickness of the ground can be reduced.

In the case where the contrast between the luminance value of the image reflected from the normal pattern and the luminance value of the image reflected from the defective pattern depends on wavelength, a waveband may be selected by the wavelength-selective filters such that the contrast between the luminance value of the image reflected from the normal pattern and the luminance value of the image reflected from the defective pattern is relatively large and such that interference fringes each of which is generated in each wavelength are canceled to reduce the influence of the unevenness of the film thickness of the ground.

Thus, even if the unevenness of the film thickness is generated in the ground, the influence of the unevenness of the film thickness can be reduced to perform a good defect inspection of the repetitive pattern 22 in the surface by illuminating the specimen 20 with the illumination light L1 including the plural emission line spectra. Because the illumination light L1 includes the plural emission line spectra, a wavelength having a high contrast compensates for a wavelength having a low contrast. The same effect can be obtained not only in the case where the illumination light L1 includes discrete spectra but also in the case where the illumination light L1 includes continuous spectrum.

Because the influence of the unevenness of the film thickness of the ground can be reduced, the surface inspecting apparatus of the second embodiment is useful to defect inspection of a process in which the repetitive pattern 22 is formed at a small area (ground has a large exposed area) in each shot area 21 (FIG. 2) of the specimen 20.

Figure 15:
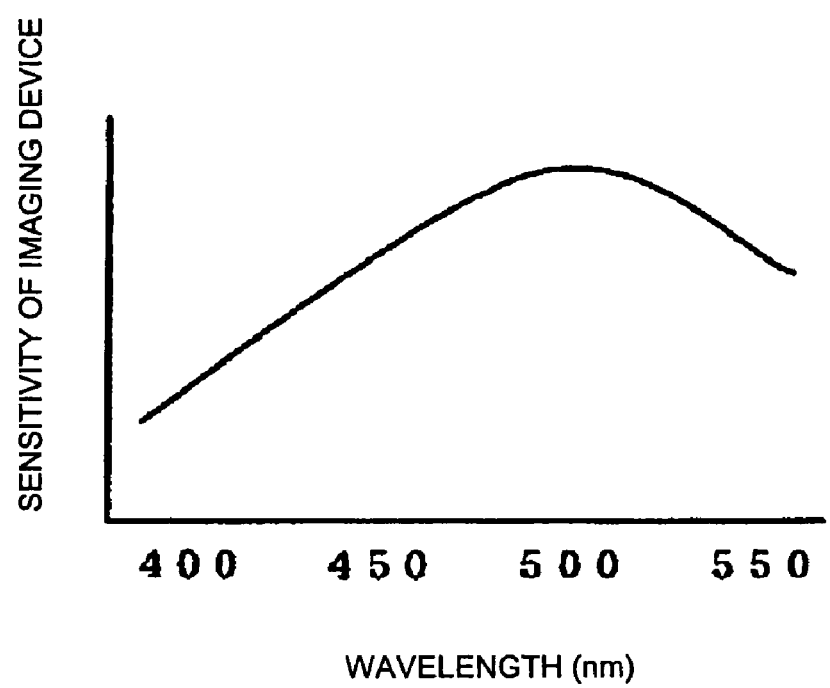
FIG. 15 is a view showing a wavelength characteristic of sensitivity of an imaging device 39.

The sensitivity of the imaging device 39 generally depends on wavelength λ. For example, as shown in FIG. 15, the sensitivity becomes the maximum at the wavelength near the 500 nm, and the sensitivity is lowered on both sides of the wavelength near the 500 nm. FIG. 15 shows the sensitivity of 400 nm to 550 nm by way of example. The light intensity of the illumination light L1 can be adjusted at each wavelength according to a wavelength characteristic of the sensitivity of the imaging device 39, which allows the influence of the unevenness of the film thickness of the ground to be reduced more effectively.

The emission line spectra (e line, g line, and h line of FIG. 14) included in the wavelength range of FIG. 15 in the light emitted from the light source 31 will be described as an example of adjustment of the light intensity of the illumination light L1 at each wavelength. When a spectral transmission factor of the wavelength-selective filter 3 is kept constant in a transmission band while the wavelength-selective filter 32 selectively transmits the e line, g line, and h line, the illumination light L1 exhibits the spectral intensity of the e line, g line, and h line as shown in, for example, FIG. 16.

Figure 16:
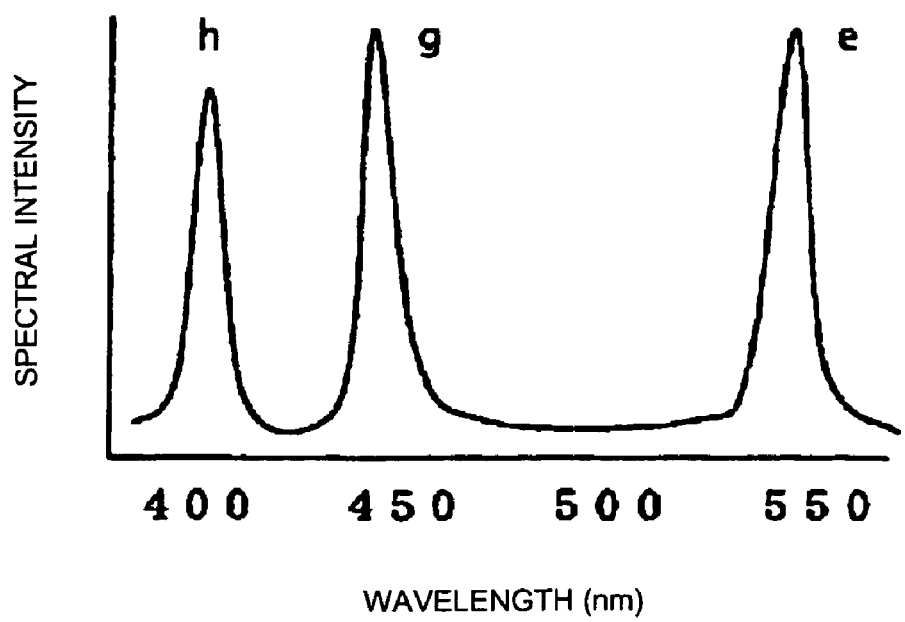
FIG. 16 is a view explaining spectral intensity (before correction) of each wavelength of the illumination light L1.
Figure 17:
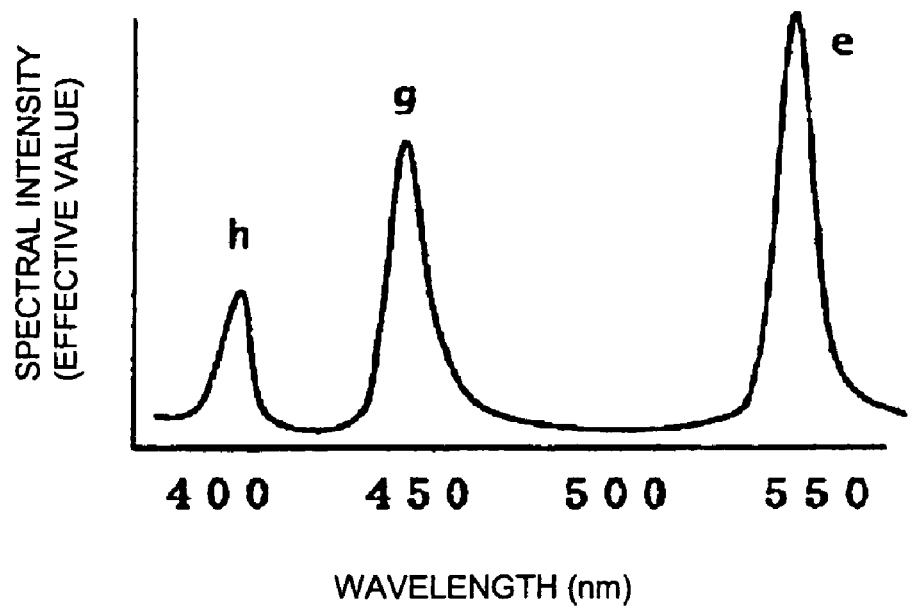
FIG. 17 is a view explaining effective intensity (before correction) after the imaging device 39 accepts light.

At this point, the elliptically polarized light L2 is generated from the specimen 20 illuminated with the illumination light L1, and the elliptically polarized light L2 exhibits the spectral sensitivity similar to that of FIG. 16 for the wavelengths λ (e line, g line, and h line). When the imaging device 39 having the sensitivity characteristic shown in FIG. 15 accept the elliptically polarized light L2, the light intensity (hereinafter referred to as "effective intensity") is lowered on shorter wavelengths as shown in FIG. 17. Therefore, the interference fringes of the wavelengths λ affected by the unevenness of the film thickness of the ground are insufficiently cancelled on the short wavelength side.

Figure 18:
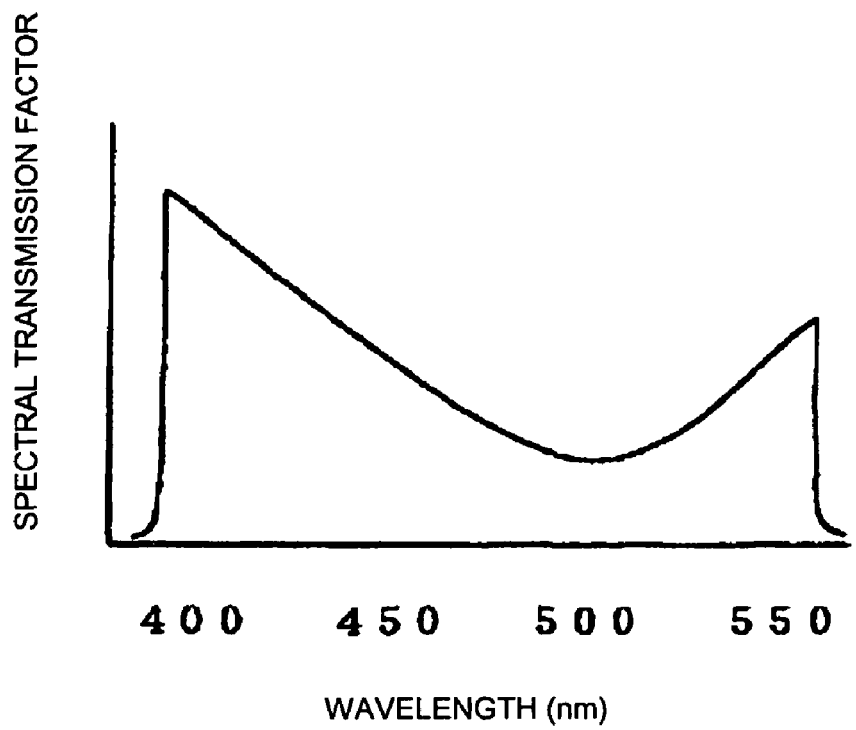
FIG. 18 is a view showing an example of a spectral transmission factor of a wavelength-selective filter 32.
Figure 19:
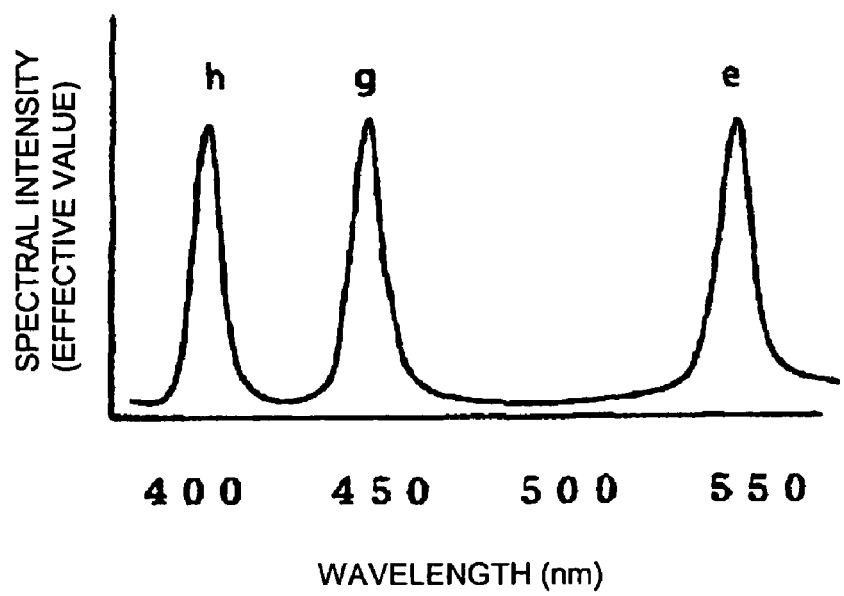
FIG. 19 is a view explaining effective intensity (after correction) after the imaging device 39 accepts the light.

In consideration of the wavelength characteristic (FIG. 15) of the sensitivity of the imaging device 39, the spectral transmission factor in the transmission band a of the wavelength-selective filter 32 is set so as to be lowered at the wavelength near 500 nm and to be increased on both the sides of the wavelength near 500 nm as shown in FIG. 18. Therefore, the light intensity of the illumination light L1 at each wavelength λ (e line, g line, and h line) is adjusted according to the spectral transmission factor (FIG. 18) of the wavelength-selective filter 32, and the effective intensity can be kept constant in each wavelength λ (e line, g line, and h line) as shown in FIG. 19 after the imaging device 39 accepts the elliptically polarized light L2.

Accordingly, the interference fringes affected by the unevenness of the film thickness of the ground can sufficiently be canceled at each wavelength λ, and the influence of the unevenness of the film thickness of the ground can be reduced more effectively. When the effective intensity is kept constant in each wavelength λ after the imaging device 39 accepts the elliptically polarized light L2, the influence of the unevenness of the film thickness of the ground can be reduced most effectively. However, the present invention is not limited to the constant effective intensity. Alternatively, even if the effective intensity is not kept constant in each wavelength λ after the imaging device 39 accepts the elliptically polarized light L2, the influence of the unevenness of the film thickness of the ground can be improved, when the light intensity of the illumination light L1 is adjusted at each wavelength λ such that the wavelength characteristic of the sensitivity of the imaging device 39 is corrected.

Wavebands (FIG. 14) selected by the wavelength-selective filters 32 are not limited to the wavebands α, β, and λ. As long as the influence of the unevenness of the film thickness can be reduced, light having a waveband (for example, 240 nm to 313 nm) shorter than the j line may be used, or light having a waveband longer than the e line may be used. The number of wavelengths included in the illumination light L1 is not limited three, but two wavelengths or at least four wavelengths may be included in the illumination light L1. A wavelength at which the contrast is hardly increased without an influence of the unevenness of the film thickness may be removed from the wavelengths selected by the wavelength-selective filter.

(Modifications)

In the embodiment, the wavelength-selective filter 32 simultaneously selects the light beams having the plural wavelengths to obtain an image combined by the polarization components of the plural wavelengths. However, the present invention is not limited to the second embodiment. The images having different wavelengths are obtained and combined by image processing, which allows the influence of the unevenness of the film thickness of the ground to be also reduced. At this point, the combination can be performed after the luminance value of the image at each wavelength is multiplied by a predetermined factor according to the sensitivity of the imaging device.

In the case where the contrast between the luminance value of the image reflected from the normal pattern and the luminance value of the image reflected from the defective pattern depends on wavelength, the combination may be performed after a luminance value of an image at each wavelength is multiplied by a predetermined factor such that the contrast between the luminance value of the image reflected from the normal pattern and the luminance value of the image reflected from the defective pattern is relatively large and such that interference fringes each of which is generated in each wavelength are canceled to reduce the influence of the unevenness of the thickness of the ground.

Although the stage 11 has the tilt mechanism in the embodiments, the present invention is not limited to the embodiments. When the specular reflection light is accepted without providing the tilt mechanism, the apparatus configuration is simplified because the tilt mechanism is eliminated.

The present invention is not limited to the embodiments in which only the stage 11 has the tilt mechanism. At least two of the illumination system 13, the light acceptance system 14, and the specimen 20 may be rotated about the tilt axes. Therefore, the incident angle θ of the illumination light L1 can be changed with respect to the specimen 20, and a reflectance is varied by the change in incident angle θ, which allows the change in surface of the specimen 20 to be detected more easily.

Although the specimen is rotated by the rotation of the stage in the embodiments, the present invention is not limited to the embodiments. It is only necessary to relatively rotate the angle formed between the incident plane of the illumination light and the pattern, and the illumination system 13 and the light acceptance system 14 may be rotated about the normal of the stage 11.

In the embodiments, because the stage 11 has the tilt mechanism, an inspection in which diffracted light is utilized can be performed. In such cases, the stage 11 may be rotated such that repetitive direction of the pattern is set to zero degree, and the stage 11 may appropriately be tilted such that the diffracted light is incident to the light acceptance system 14. During the inspection with diffracted light, the polarizing plate and the corrector plate may be arbitrarily inserted and retracted by the insertion and retraction mechanism according to a pattern to be inspected.

Although the repetitive pattern is described in the embodiments, the present invention can be applied to the object such as a logic wafer in which the repetitive pattern hardly exists. The logic circuit is basically formed by the straight-line pattern, and the orientation of the straight line is equalized to that of the repetitive pattern. Therefore, it is believed that the repetitive pattern is identical to the logic pattern in the action in which linearly polarized light used in the illumination is converted into the elliptically polarized light. In such cases, the stage can be rotated such that the incident plane of the illumination light is set to a predetermined angle with respect to the straight-line direction of the pattern.

In the embodiments, the two-dimensional sensor such as CCD is used as the imaging device 39. Alternatively, a one-dimensional sensor may be used. In such cases, the one-dimensional sensor which is of the imaging device and the stage on which the semiconductor wafer (or liquid crystal display substrate) which is of the specimen is placed are relatively moved, the one-dimensional sensor scans the whole surface of the semiconductor wafer (or liquid crystal display substrate), and the image of the whole surface may be captured.

In each process of the semiconductor wafer production, desirably a relationship between the wavelength and the unevenness of the film thickness or a relationship between the wavelength and the magnitude of the contrast between the normal pattern and the defocus pattern has been previously obtained using a test wafer in which the normal pattern and the defocus pattern are mixed, and the optimum condition is set based on the relationship previously obtained from the inspection in each process.

The invention claimed is:

1. A surface inspecting apparatus comprising:
    illumination means for illuminating a repetitive pattern formed in a surface of a specimen with linearly polarized light;
    setting means for setting an angle at a predetermined value except for zero, the angle being formed between a direction in the surface of an incident plane of the linearly polarized light and a repetitive direction of the repetitive pattern;
    extraction means for extracting a polarization component perpendicular to a vibration plane of the linearly polarized light from light generated in a specular reflection direction from the repetitive pattern;
    light acceptance means for accepting the light extracted by the extraction means and supplying light intensity of the specular reflection light; and
    detection means for detecting a defect of the repetitive pattern based on the light intensity of the specular reflection light supplied from the light acceptance means,
    wherein the setting means sets the angle formed between the direction in the surface of the incident plane of the linearly polarized light and the repetitive direction of the repetitive pattern such that a contrast becomes maximum, the contrast is an absolute value (1−[(luminance value of image reflected from defective pattern (measured value))/(luminance value of image reflected from normal pattern (measured value))]).

2. The surface inspecting apparatus according to claim 1, wherein the linearly polarized light includes light beams having a plurality of different wavelengths.

3. The surface inspecting apparatus according to claim 2, comprising intensity adjusting means for adjusting an intensity distribution of the linearly polarized light including the light beams having the plurality of different wavelengths according to sensitivity of the detection means.

4. The surface inspecting apparatus according to claim 2, comprising wavelength selecting means for selecting the plurality of different wavelengths according to a difference between light intensity of a normal portion of the surface and light intensity of a defective portion of the surface, generated in each wavelength, and light intensity of light from the specimen of each wavelength.

5. The surface inspecting apparatus according to claim 1, wherein the illumination means includes wavelength selecting means for changing a wavelength of the linearly polarized light,
    the light intensity of the specular reflection light is obtained while a wavelength of the linearly polarized light emitted from the illumination means is changed, and
    the defect of the repetitive pattern is detected based on light intensity obtained by combining the light intensity of the specular reflection light of each wavelength.

6. The surface inspecting apparatus according to claim 5, wherein a combination ratio of light intensity obtained in each wavelength is changed according to sensitivity of the detection means.

7. The surface inspecting apparatus according to claim 5, wherein the combination ratio of the light intensity obtained in each wavelength is changed according to a difference between light intensity of a normal portion of the surface and light intensity of a defective portion of the surface, generated in each wavelength, and light intensity of light from the specimen of each wavelength.

8. The surface inspecting apparatus according to claim 1, wherein an angle $\phi$ formed between the direction in the surface of the incident plane of the linearly polarized light and the repetitive direction of the repetitive pattern is set so as to satisfy the following equation:

$\phi=22.5°+45\times N°$ (N is an integer of one of 0 to 6).

9. The surface inspecting apparatus according to claim 1, comprising first rotary means for relatively rotating the specimen, the illumination means and the light acceptance means about an axis orthogonal to the surface.

10. The surface inspecting apparatus according to claim 9, comprising second rotary means for rotating the specimen about an axis, the axis being orthogonal to the incident plane and included in the surface.

11. The surface inspecting apparatus according to claim 9, comprising second rotary means for rotating at least two of the illumination means, the light acceptance means, and the specimen about an axis, the axis being orthogonal to the incident plane and included in the surface.

* * * * *